United States Patent [19]

Kanojia et al.

[11] 3,986,952
[45] Oct. 19, 1976

[54] ISOLATION OF UTERO-EVACUANT SUBSTANCES FROM PLANT EXTRACTS

[75] Inventors: Ramesh M. Kanojia, Somerville; Richard E. Huettemann, Hazlet, both of N.J.

[73] Assignee: Ortho Pharmaceutical Corporation, Raritan, N.J.

[22] Filed: Nov. 17, 1975

[21] Appl. No.: 632,552

[52] U.S. Cl. .................................. 210/31 C; 55/67
[51] Int. Cl.² ........................................ B01D 15/08
[58] Field of Search ................... 210/21, 22, 31 C; 55/67; 424/195

[56] References Cited
OTHER PUBLICATIONS

Introduction to Modern Liquid Chromatography by Snyder and Kirkland, John Wiley and Sons, New York, N. Y. pp. 374–377.
Thin Layer Chromatography An Annotated Bibliography; 1964–1968 by Haywood, Ann Arbor Science Pub. Inc. Ann Arbor, Mich.
Abstract of Lundstrom et al. of J. Chromatog. 30, 271–272(1967), p. 204.
Abstract of Eglington et al., Science 156, 1322–1335 (1967) p. 96.
1969 Edition Gas Chromatography Abstracts by Knapman et al., The Institute of Petroleum, London, Eng. Abstract 10 of Ina et al., Tetrahedon Letters 1968 (23) 2777–2780. p. 2.

*Primary Examiner*—John Adee
*Attorney, Agent, or Firm*—Benjamin F. Lambert

[57] ABSTRACT

A method of obtaining utero-evacuant substances from the zoapatle plant is described. The method involves the isolation and purification of biologically active compounds from the zoapatle plant by chromatography over silicic acid impregnated with silver nitrate.

6 Claims, No Drawings

ISOLATION OF UTERO-EVACUANT SUBSTANCES FROM PLANT EXTRACTS

In co-pending application Ser. No. 547,415, filed Feb. 6, 1975, there is described a method of isolating and purifying extracts of the zoapatle plant which leads to purified compounds having useful biological activity. The method involves chromatography of the crude material through a column of adsorbent material followed by chromatography through a column of an organic polymeric gel. The present invention relates to a method of isolating and purifying the biologically active materials present in the zoapatle plant by chromatography over silicic acid impregnated with silver nitrate.

The zoapatle plant is a bush about 2 m. high that grows wild in Mexico. Botanically it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, third edition, Ediciones Botas (1944).

The plant has been used for centuries in the form of a "tea" or other crude aqueous preparations primarily as a labor inducer or menses inducer for humans. Its use has been documented in the literature, but definitive chemical and pharmacological studies have not been performed.

In the current folk use of the zoapatle plant, the user typically drinks a bitter tasting "tea" brewed from the leaves of the plant by boiling them with water in the same manner used to prepare a hot beverage. She normally does this after having missed a menstrual period and thus is presumably pregnant, although it is known that many frankly pregnant women use the tea to terminate an unwanted pregnancy. The "tea" obviously contains a mixture of complex materials, many of which may be undesirable and unnecessary to produce the desired effect. Natural plant substances are generally known to be exceedingly complex in their composition. Many compounds of similar chemical and physical properties, as well as those with strikingly dissimilar properties, are normally found in these substances and generally present a difficult separation and identification task.

In the above mentioned co-pending application, a method is described for purification of crude extracts from the zoapatle plant which results in a material having biological activity and containing at least three components. This semi-purified material is the starting material for the present invention.

By means of the present invention, two chemically distinct compounds having utero-evacuant properties are obtained by chromatography of the semi-purified material on silicic acid impregnated with silver nitrate. By utero-evacuant is meant an agent causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

In carrying out the process of the present invention, the amount of silver nitrate impregnated on the silicic acid may vary from about 1 to about 30%. It is preferred, however, to use a mixture of silicic acid impregnated with about 10% silver nitrate. Silicic acid mixtures with silver nitrate can be prepared by first making a slurry of silicic acid with a solution of silver nitrate in a suitable solvent. Solvents which may be employed include water or lower aliphatic alkanols such as methanol, ethanol or propanol; lower aliphatic ketones such as acetone, methyl ethyl ketone, diethyl ketone and the like and lower aliphatic nitriles such as acetonitrile. Silicic acid is added in small portions to a solution of silver nitrate. The solvent is removed from the resultant slurry by some suitable means until the residue is reduced to a free flowing powdery solid. This material is then dried for several hours, preferably in the absence of light. The dried silicic acid-silver nitrate mixture is then used to prepare a chromatographic support such as, for example, a column, preparative plate, preparative high performance liquid chromatography or preparative gas chromatography. For purposes of illustration, the invention will be described in terms of column chromatography. It should be understood, however, that any suitable support for the adsorbent may be employed.

In carrying out the method of this invention, a sample of the semi-purified utero-evacuant material dissolved in a suitable solvent, such as benzene, toluene, diethyl ether, hexane and the like, is added to a column of silicic acid impregnated with silver nitrate. The column may be prepared dry, but it is preferred to prepare the column in a solvent. The solvent employed is generally the solvent used to dissolve the utero-evacuant material. The column is then eluted with solvent and several fractions are collected. Suitable solvents which can be employed to elute the column include polar solvents such as methanol, ethanol, isopropanol, acetone, and ethyl acetate, relatively non-polar solvents such as chloroform, methylene chloride, benzene, toluene, diethyl ether, diisopropyl ether, hexane, cyclohexane and the like. Various combinations of these solvents may be employed where desirable. Where an increased rate of flow is desired, the column can be eluted with the application of low pressure, up to about 10 psi. This can be accomplished through application to the column of an inert gas such as nitrogen, for example. The composition of the fractions is monitored by thin layer chromatography on silicic acid impregnated with silver nitrate or by gas chromatography.

As a result of the above procedure, two chemically distinct utero-evacuant compounds are obtained as evidenced by gas chromatography and spectral analysis. Minor impurities present as silver compounds can be removed from the purified compounds by filtering a solution of the compound in a solvent such as benzene or methylene chloride, for example, through a short column or pad of celite or silicic acid. The utero-evacuant properties of the isolated materials are determined by measuring the extent of uterine contractions and the degree to which pregnancy is interrupted in female animals.

The purified utero-evacuant compounds are effective when administered in doses ranging from 1.0 mg. to about 100 mg./kg. The actual dosage employed will depend upon the species of animal to which the compound is administered. The compounds can be administered in formulations prepared according to acceptable pharmaceutical practices. Suitable formulations would include solutions, suspensions and solid dosage forms.

The following describes the invention in greater particularity and is intended to be a way of illustrating but not limiting the invention

PREPARATION OF STARTING MATERIAL

Zoapatle leaves (10 kg.) and water (30 gallons) are added to a 100 gallon steam-jacketed stainless steel tank. The mixture is heated at 98°–100° C for 2.5 hours with periodic stirring. The hot mixture is filtered through gauze to afford a clear dark tea (about 25 gallons). The solid residue in the tank is washed with hot water (4 gallons), filtered, and the filtrate combined with the tea obtained above. The combined aqueous extracts are extracted with ethyl acetate (30 gallons). The mixture is stirred vigorously and allowed to settle. The top frothy layer is siphoned off to break the emulsion, and as much ethyl acetate separated as possible. Additional acetate (20 gallons) is added to the mixture and the above process is repeated. The combined ethyl acetate extracts are evaporated at 50° C under vacuum. The residue is extracted with 3 portions of hot (75°–80°) benzene (10 liters total. The benzene extracts are evaporated at 50° C under vacuum and the residue is washed three times with refluxing hexane (a total of 8 liters). The hexane washed residue is dissolved in acetone (2 liters), Nuchar (10 g.) is added, and the mixture is stirred 1 hour at room temperature. The charcoal is removed by filtration, and the filtrate evaporated by distillation at 30° C under vacuum to afford the crude extract (69 g.).

The crude extract (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral silicic acid packed in chloroform. The column is eluted with chloroform, chloroform-isopropanol mixtures, and 110 fractions are collected. The fractions are evaporated to dryness in vacuo at a temperature below 40° C. The column is eluted as follows:

| Fraction | Volume/Fraction (ml.) | Eluent | |
|---|---|---|---|
| 1–7 | 650 | $CHCl_3$ | |
| 8–30 | 500 | isopropanol:$CHCl_3$ | (1:41.7) |
| 31–60 | 500 | isopropanol:$CHCl_3$ | (1:33.3) |
| 61–105 | 500 | isopropanol:$CHCl_3$ | (1:28.6) |
| 106–110 | 500 | isopropanol:$CHCl_3$ | (1:25) |

The composition of the fractions is monitored by thin layer chromatography [silica gel, isopropanol-chloroform (1:12.5)] and by gas chromatography — 3% OV17 [methyl silicone:phenyl silicone (1:1)] column using a programmed run (150°–250°). Fractions Nos. 78–84 are combined and the solvent removed in vacuo to afford an oily residue of the semi-purified material (5.1 g.) which contains at least three components as indicated by gas chromatography.

EXAMPLE

The semi-purified material (505 mg.) obtained as described above is dissolved in benzene (2 ml.) and the solution is added to a column of silicic acid impregnated with 10% silver nitrate (25 g., 20 mm. ID × 6 inches) prepared in benzene. The column is eluted under a low pressure of nitrogen (up to 7 psi) with increasing proportions of acetone in benzene. A total of 71 fractions (25 ml. each) is collected as indicated below:

| Fraction | Total Volume | Eluent | |
|---|---|---|---|
| 1–18 | 450 ml. | acetone:benzene | (5:95) |
| 19–28 | 250 ml. | acetone:benzene | (7.93) |
| 29–38 | 250 ml. | acetone:benzene | (10:90) |
| 39–71 | 825 ml. | acetone:benzene | (12:88) |

The composition of the fractions is monitored by thin layer chromatography (20% silver nitrate impregnated silica GF, acetone:benzene, 50:50 or isopropanol:acetone:$CHCl_3$, 1:30:50) and by gas chromatography — 3% OV17 [methyl silicone:phenyl silicone (1:1)] column using a programmed run (150°–250°).

Fractions 33–39 are evaporated to give an oil (73.3 mg., 14.5%) having the following spectral data:

I.R. (Neat) 2.90 $\mu$, 5.96 $\mu$ and 6.21 $\mu$

N.M.R. $_{TMS}{}^{CDCl_3}$ 6.11, 5.48, 4.25, 4.13, 3.56, 2.11, 2.08, 1.48, 1.13 and 1.01 ppm.

Fractions 46–56 are evaporated to give an oil (122.7 mg., 24.2%) having the following spectral data:

I.R. (Neat) 2.91 $\mu$ and 5.88 $\mu$

N.M.R. $_{TMS}{}^{CDCl_3}$ 5.41, 4.26, 4.15, 3.58, 3.18, 2.18, 1.76, 1.67, 1.15 and 1.04 ppm.

PREPARATION OF $AgNO_3$-SILICIC ACID MIXTURE

Silicic acid (250 g.) is added in small portions to a solution of silver nitrate (25 g.) in hot methanol (~700 ml.) until a slurry is obtained. The solvent is removed from the slurry on a rotary evaporator at 50°–60° in vacuo until the residue is reduced to a free flowing powdery solid. This material is spread on a tray and dried in the absence of light in an oven at 120° for 17 hrs. Prior to use the cooled, dried material is stored in a glass container protected from light and moisture.

The following general procedure is employed to detect uterine contractions in female animals.

PROCEDURE I

Mature female New Zealand rabbits are anesthetized with sodium pentobarbital and ovariectomized. Following a recovery period of 1 week, the rabbits are treated with 5 $\mu$g./day s.c. of 17$\beta$-estradiol for 6 consecutive days, followed by treatment with 1.0 mg./day s.c. of progesterone for 7 consecutive days. The uterus and oviducts of the rabbits are perfused 72 hours after the last dose of progesterone according to the method of Heilman, et al., (Fertil. Steril. 23:221–229) with slight modifications. The oviduct and uterus are perfused at a rate of 53 $\mu$l./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous administration of the compound obtained from Fractions 46–56 is effective in inducing uterine contractions and relaxing the oviduct in 72-hour progesterone withdrawn rabbits in a dose range of 1.0–4.0 mg./kg. The compound obtained from Fractions 33–39 is effective when administered in a dose range of from 25–40 mg./kg.

The following general procedure is employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5–6 females are given test materials intra-peritoneally in the vehicle described in Procedure I on day 22 of gestation. Pigs are sacrificed between the 25th and 45th day of gestation and examined for evidence of resorption or abortion.

Intra-peritoneal administration of the material obtained from Fractions 46–56 is effective in interrupting pregnancy when administered in a dose range from 25–85 mg./kg.

What is claimed is:

1. The method of purifying extracts containing materials obtained from the zoapatle plant which comprises the steps of:

dissolving the mixture of semi-purified materials in a water-immiscible organic solvent, chromatographing the resultant solution on silicic acid impregnated with silver nitrate, eluting the silicic acid with a mixture of polar and non-polar organic solvents and collecting the fractions containing the materials.

2. The method of claim 1 wherein the zoapatle plant is *Montanoa tomentosa* or *Montanoa floribunda*.

3. The method of claim 1 wherein the water-immiscible solvent is selected from an aromatic hydrocarbon, a chlorinated hydrocarbon or an aliphatic ether.

4. The method of claim 3 wherein the organic solvent is selected from benzene, chloroform and ether.

5. The method of claim 1 wherein the silicic acid is impregnated with from 1–30% of silver nitrate.

6. The method of claim 1 wherein the mixture of polar and non-polar solvents comprises a mixture of acetone and benzene.

* * * * *